US011793533B2

(12) United States Patent
Barthelmes et al.

(10) Patent No.: US 11,793,533 B2
(45) Date of Patent: Oct. 24, 2023

(54) SURGICAL INSTRUMENT HAVING TERMINAL REGION THROUGH WHICH FLOW CAN OCCUR

(71) Applicant: Aesculap AG, Tuttlingen (DE)

(72) Inventors: Sven Barthelmes, Emmingen-Lipptingen (DE); Stefanie Schabert, Aldingen (DE)

(73) Assignee: Aesculap AG, Tuttlingen (DE)

( * ) Notice: Subject to any disclaimer, the term of this patent is extended or adjusted under 35 U.S.C. 154(b) by 249 days.

(21) Appl. No.: 17/438,549

(22) PCT Filed: Mar. 5, 2020

(86) PCT No.: PCT/EP2020/055910
§ 371 (c)(1),
(2) Date: Sep. 13, 2021

(87) PCT Pub. No.: WO2020/182625
PCT Pub. Date: Sep. 17, 2020

(65) Prior Publication Data
US 2022/0151648 A1 May 19, 2022

(30) Foreign Application Priority Data

Mar. 14, 2019 (DE) ..................... 10 2019 106 512.7

(51) Int. Cl.
*A61B 17/28* (2006.01)
*A61B 90/00* (2016.01)
(52) U.S. Cl.
CPC .. *A61B 17/2816* (2013.01); *A61B 2017/2808* (2013.01); *A61B 2017/2837* (2013.01); *A61B 2090/0813* (2016.02)
(58) Field of Classification Search
CPC ..... A61B 17/04; A61B 17/0483; A61B 17/12; A61B 17/28; A61B 17/2812;
(Continued)

(56) References Cited

U.S. PATENT DOCUMENTS 2,305,156 A * 12/1942 Grubel ............... A61B 17/2816
403/114
3,763,726 A * 10/1973 Hildebrand ........ A61B 17/2816
81/416
(Continued)

FOREIGN PATENT DOCUMENTS

DE 2061539 A1 8/1972
DE 8316305 U1 10/1983
(Continued)

OTHER PUBLICATIONS

Written Opinion received in International Application No. PCT/EP2020/055910 dated Jun. 3, 2020, with translation, 10 pages.
(Continued)

*Primary Examiner* — Sarah W Aleman
(74) *Attorney, Agent, or Firm* — Christopher A. Rothe; Culhane Meadows PLLC

(57) ABSTRACT

A branch-crossed surgical instrument includes a female branch and a male branch, each branch having a terminal portion over the longitudinal extension thereof. The terminal portion of the female branch is passed through by a passage opening, which has a distal and a proximal longitudinal end surface, each having two outer edges and adjusted to receive the terminal portion of the male branch such that the two terminal portions form a plug-through closure in an assembly position of the instrument. The passage opening has a length, wherein the outer edges of the longitudinal end surfaces are exposed in all relative positions of the two branches, in particular in a completely closed position and/or in a completely opened position of the instrument, and not covered by the male branch.

7 Claims, 3 Drawing Sheets

(58) Field of Classification Search
CPC .............. A61B 17/2816; A61B 17/282; A61B 17/2833; A61B 17/2841; A61B 17/30; A61B 17/3201; A61B 2017/2808; A61B 2017/2837; A61B 2017/2926; A61B 2017/2939; A61B 2017/2947; A61B 2018/1457; A61B 2090/0813; A61C 3/14; A61C 3/16; B25B 7/00; B25B 7/02; A41H 37/066

See application file for complete search history.

(56) References Cited

U.S. PATENT DOCUMENTS

| | | | | |
|---|---|---|---|---|
| 3,952,749 | A * | 4/1976 | Fridolph | B25B 7/06 606/208 |
| 2003/0181944 | A1 * | 9/2003 | Propp | A61B 17/2816 606/205 |
| 2007/0265657 | A1 * | 11/2007 | Sexton | A61B 17/28 606/208 |
| 2007/0276431 | A1 | 11/2007 | Swartz et al. | |
| 2018/0000536 | A1 * | 1/2018 | Becker | A61B 18/1445 |
| 2019/0150965 | A1 * | 5/2019 | Barthelmes | A61B 17/2816 |
| 2020/0383695 | A1 | 12/2020 | Weisshaupt et al. | |

FOREIGN PATENT DOCUMENTS

| | | |
|---|---|---|
| DE | 102016111892 A1 | 1/2018 |
| DE | 102017105706 A1 | 9/2018 |
| WO | 2016169037 A1 | 10/2016 |

OTHER PUBLICATIONS

Search Report received in German Application No. 10 2019 106 512.7 dated Dec. 3, 2019, with translation, 16 pages.

Search Report received in International Application No. PCT/EP2020/055910 dated Jun. 3, 2020, with translation, 6 pages.

\* cited by examiner

SURGICAL INSTRUMENT HAVING TERMINAL REGION THROUGH WHICH FLOW CAN OCCUR

CROSS-REFERENCE TO RELATED APPLICATIONS

This application is the United States national phase entry of International Application No. PCT/EP2020/055910, filed Mar. 5, 2020, and claims the benefit of priority of German Application No. 10 2019 106 512.7, filed Mar. 14, 2019. The contents of International Application No. PCT/EP2020/055910 and German Application No. 10 2019 106 512.7 are incorporated by reference herein in their entireties.

FIELD

The invention relates to a surgical instrument of cross-branched design having a male branch and a female branch pivotably held together in an assembly position of the instrument via a box-lock mechanism, for which purpose the female branch thereof forms in its terminal region a box-lock opening in which a terminal region of the male branch can be pivotably received.

BACKGROUND

In the preparation and performance of surgical treatments, various surgical instruments are used depending on the treatment, including, for example, clamps for securing surgical drapes, cables or tubes and forceps for various applications. Clamps and forceps are usually instruments with two branches crossing each other, similar to the scissors design, and are hinged to each other in the assembly position in their terminal region and/or are held together via a box-lock mechanism.

After treatment or respectively before use, all instruments have to be cleaned and sterilized. In particular, care must be taken to ensure that cleaning/sterilization is carried out at all accessible points of the instrument in order to ensure maximum patient safety. For this purpose, instruments with two crossing branches are usually brought into their maximum open position before they are then subjected to the further cleaning/sterilization process, for example, they are placed in a sterile container and heat-sterilized under the influence of heat or chemically treated in a cleaning/sterilization bath.

Surgical instruments of cross-branched design, for example clamps or forceps, which are connected to each other by a box-lock mechanism, are already known. The two branches each have a terminal region which, viewed in the longitudinal direction of the branches, is arranged between a distal effector portion (e.g. gripping surface) and a proximal gripping portion. The terminal region of the female branch has an elongated passage opening that is provided to receive the terminal region of the male branch. For assembly, the passage opening is first widened, for example with the aid of a mandrel, in order to pass the male branch through, so that the terminal region of the male branch is located in the passage opening. The expanded terminal region is then deformed back into its original shape. For hinging the two branches to each other, either a bolt bearing opening mechanism can be arranged on the walls of the terminal regions facing each other, or the terminal regions of the two branches have a coaxial passage hole into which a separate locking pin is inserted, around whose longitudinal axis the two branches are then rotatably secured to each other. Alternatively, the terminal region can also be designed as in DE 10 2017 105 706 A1 with part-circular grooves and projections.

Surgical forceps known in the prior art are disclosed, for example, in the German patent application DE 2061 539 with two branches which are connected to each other via a box-lock mechanism, wherein a projection is provided on each of the opposite inner surfaces of the box-lock opening of the female branch, wherein these projections are arranged coaxially to each other and each one engages in a complementary recess on the terminal region of the male branch in order to hold the latter pivotably in the box-lock opening.

International patent application WO 2016/169037 A1 also discloses surgical forceps with two branches held together by a box-lock mechanism.

For stability reasons, the passage opening in the terminal region of the female branch is usually designed with a length in which the terminal region of the male branch can be just barely received in the fully closed position of the instrument. As a result, in the fully open position of the instrument, the outer surface of the male branch abuts the outer surface of the female branch in such a way that the longitudinal ends of the passage opening on the sides facing the male branch are covered by the outer surface of the male branch, or respectively the longitudinal edges of the passage opening facing the male branch abut the outer surface of the male branch. In this way, two pockets are formed in the area of the passage opening in the maximum opening position of the instrument, that is, along the inner wall of the passage opening and the outer surface of the male branch closing the passage opening. The flow cannot pass through these pockets, which can make cleaning and/or sterilization more difficult.

Cleaning these instruments is also a known challenge. The German patent application DE 10 2016 111 892 A1 describes surgical forceps with two branches which are held together by a box-lock mechanism and whose contact surfaces in the terminal region each have a different surface structure from each other, so that the contact of the two instrument branches with each other is line-shaped and/or point-shaped and free spaces are formed between the contact lines/contact points which can be reached by a disinfectant. However, the ability of the disinfectant to flow through this design is not sufficient.

The prior art thus always has the disadvantage of inadequate disinfectability or cleanability, which represents a considerable health risk for the patient as well as for the user.

SUMMARY

The object of the present invention is thus to overcome or at least reduce the disadvantages of the prior art and, in particular, to provide a surgical instrument of cross-branched design whose branches are held together via a box-lock mechanism and through which a cleaning and/or sterilization medium can flow easily in any opening position of the assembled instrument or respectively any relative position of the two branches.

A basic idea of the invention is to provide a surgical instrument of cross-branched design with a male and a female branch held together via a box-lock mechanism in which the box-lock slot adopts a widened shape.

Specifically, a surgical instrument of cross-branched design is provided having a female branch and a male branch, each having a terminal portion along their longitudinal extent, and the terminal portion of the female branch being pierced by a passage opening having a distal and a proximal longitudinal end surface each, having two outer edges and being adapted to receive the terminal portion of the male branch, so that the two terminal portions form a box-lock mechanism in an assembly position of the instrument. The passage opening has a length at which the (all) outer edges of the longitudinal end surfaces are exposed (at least in sections) and are not covered by or contacted by the male branch or its outer surface (at least in sections) in all relative positions of the two branches, in particular in a fully closed position and/or in a fully open position of the instrument.

In particular, the passage opening may further form two opposite (essentially parallel) inner contact surfaces by which the two longitudinal end surfaces are connected to each other, the terminal portion of the male branch may form two outer contact surfaces facing away from each other and outer transverse surfaces connecting the two outer contact surfaces to each other, in such a way that in the box-lock mechanism in each case an inner contact surface and an outer contact surface are held rotatably against each other, and in all relative positions of the branches in each case between the proximal and the distal longitudinal end surface and an outer transverse surface, a channel through which a cleaning agent can flow is formed.

In this way, it can be ensured that a cleaning agent can flow through the surgical instrument in all positions of the branches relative to each other, and consequently a health risk for the user and the patient, which arises from residual germs or respectively impurities remaining after cleaning, is reduced. The widened dimension or length of the passage opening according to the invention prevents in particular the formation of pockets in the maximum opened state of the instrument, in which the cleaning agent accumulates instead of flowing around the branches.

'Proximal' always refers to the end facing the user of the surgical instrument, and 'distal' always refers to the end facing away from the user.

Preferably, the passage opening (in the longitudinal section of the branch) takes the form of an elongated passage hole. The longitudinal ends of the passage opening are consequently rounded, in particular in the form of semicircles. Particularly preferably, at least one longitudinal end surface, preferably both longitudinal end surfaces, of the elongated passage hole is/are beveled in each case at least to one of its outer sides of the opening, preferably in each case to both opening sides, in order to increase an opening cross section at at least one outer side of the opening.

The advantage according to the invention of enabling flow through the passage opening at its longitudinal ends can be further increased in this way.

In particular, the two terminal portions of the two branches may each be arranged between a distal effector portion and a proximal handle portion, wherein (in the assembled state of the branches or the instrument) the effector portions of the two branches each have an inner effector surface facing the other branch and the handle portions of the two branches each have an inner handle surface facing the other branch. The outer transverse surfaces of the terminal portion on the male branch may furthermore be a distal transverse surface (extending obliquely to the longitudinal extent of the branch), a proximal transverse surface (extending obliquely to the longitudinal extent of the branch), and two longitudinal surfaces oriented substantially parallel to each other (and extending parallel to the longitudinal extent of the branch), wherein the distal transverse surface adjoins the inner effector surface of the male branch and the proximal transverse surface adjoins the inner handle surface of the male branch, and the transitions from the distal transverse surface to the inner effector surface as well as from the proximal transverse surface to the inner handle surface are formed in the form of a distal or respectively a proximal rounding, which extends over the entire width of the branches.

Width in this context means the direction of extension transverse to the longitudinal axis of the branches and perpendicular to the pivot plane of the branches.

The rounding at the transition between the inner effector surface or inner handle surface and the terminal portion has the advantage of improved cleanability, since germs and dirt particles cannot adhere to it compared to an angular edge, for example, and can be easily collected and rinsed out by cleaning agents and/or a cleaning instrument.

Preferably, the effector portion and the handle portion of the male branch each have two outer surfaces facing away from each other, which adjoin the outer contact surfaces of the terminal region and, at their transitions to the outer contact surfaces, they each form a step which protrudes from the outer contact surface or respectively is offset from the outer contact surface by a predetermined radius, wherein the steps on the side of the inner effector surface are arranged distal to the distal rounding and the steps on the side of the inner handle surface are arranged proximal to the proximal rounding.

This geometric arrangement has the advantage of preventing a notch effect occurring at two edges 'falling on top of each other', for example at the transition from the distal or proximal transverse surface to the inner effector surface or respectively the inner handle surface and a step edge, and consequently providing the entire instrument with increased stability.

In particular, the terminal portion of the female branch preferably has two outer terminal surfaces extending substantially parallel to the inner contact surfaces, which, in the closed state of the instrument, are arranged at a distance from the outer surfaces of the handle portion and the effector portion of the male branch and in particular in this way form a gap.

The clear gap thus created between the outer terminal surfaces of the female branch and the grip portion or effector portion of the male branches enables improved cleaning.

BRIEF DESCRIPTION OF THE DRAWING FIGURES

The invention is described in more detail below by way of a preferred configuration example with reference to the accompanying drawing figures, which are described below.

DETAILED DESCRIPTION

Figure 1:
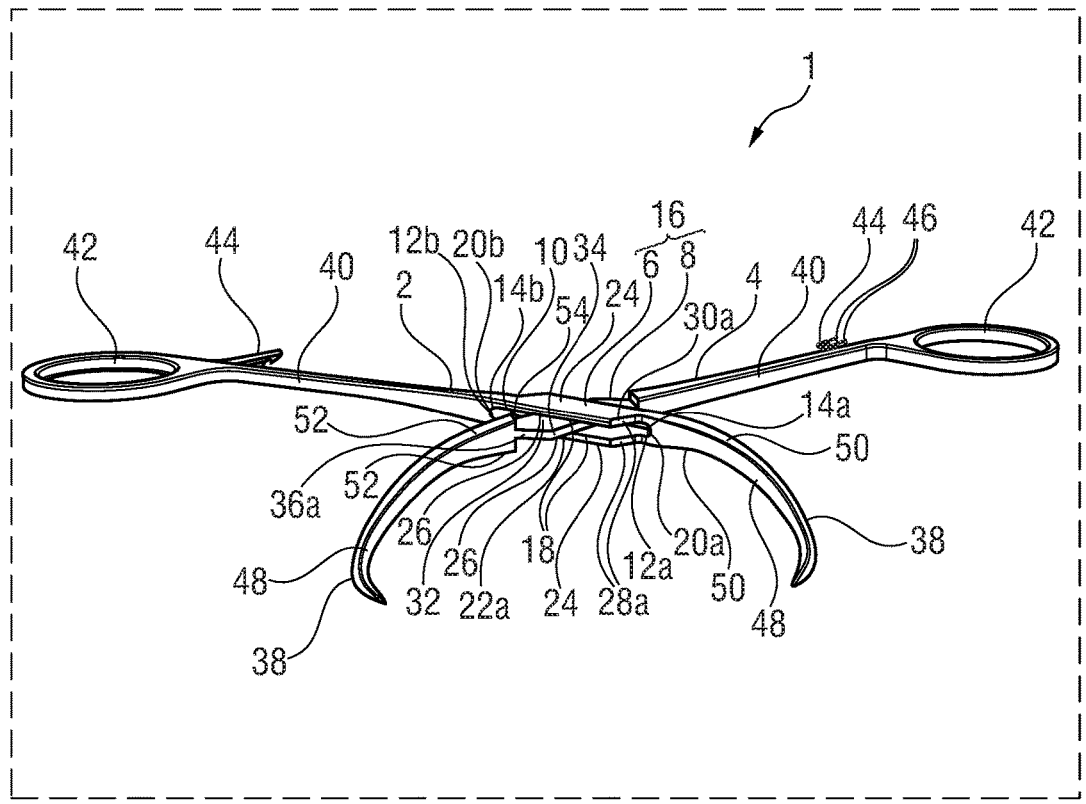
FIG. 1 shows a perspective front view of a surgical instrument in an opened state according to an embodiment of the invention.

FIG. 1 shows a perspective front view of a surgical instrument 1 according to an embodiment of the invention. A surgical instrument 1 of cross-branched design is shown having a female branch 2 and a male branch 4, each having a terminal portion 6, 8 along their longitudinal extent, and the terminal portion 6 of the female branch 2 being pierced by a passage opening 10 having a distal and a proximal longitudinal end surface 12a, b each with two outer edges 14a-d and being adapted to receive the terminal portion 8 of the male branch 4 so that the two terminal portions 6, 8 form a box-lock mechanism in an assembly position of the instrument 4. Thereby, the passage opening 10 has a length at which the outer edges 14a-d of the longitudinal end surfaces 12a, b are exposed and not covered by the male branch 4 in all relative positions of the two branches 2, 4, in particular in a fully closed position and/or in a fully opened position of the instrument 1.

In particular, the terminal region 16 of the instrument 1 can be seen in an opened state. In the terminal region 16 of the instrument 1, the terminal portion 8 of the male branch 4 (hereinafter referred to as male terminal portion 8) is located in a passage opening 10 in the terminal portion 6 of the female branch 2 (hereinafter referred to as female terminal portion 2) and is rotatably held therein. The male terminal portion 8 and the female terminal portion 6 thus form a box-lock mechanism in which the two branches 2, 4 are rotatably hinged to each other. The plane in which the branches 2, 4 can be pivoted relative to each other about the hinge (not shown) of the terminal region 16 of the instrument 1 is called the pivot plane. Here, the pivot plane is a common pivot plane of the two branches 2, 4.

In this embodiment, the passage opening 10 of the female terminal portion 8 is an elongated passage hole 10. The elongated passage hole 10 has two opposite inner contact surfaces 18 that are substantially parallel to the pivot plane. At its longitudinal ends 20a, b, the passage hole 10 has two longitudinal end surfaces 12a, b via which the inner contact surfaces 18 are connected to each other. The rounded longitudinal ends 20a, b of the elongated passage hole 10 are each beveled towards the two outer sides 22a, b of the openings of the elongated passage hole 10 (only a first outer side 22a of the opening can be seen in FIG. 1, the second outer side 22b of the opening can be seen in FIG. 2) and each increase the opening cross-section of the elongated passage hole 10 towards the two outer sides 22a, b of the openings. The female terminal portion 6 further has two outer terminal surfaces 24 extending substantially parallel to the pivot plane, each having two longitudinal edges 26 extending in the longitudinal direction of the branches 2, 4 and two transverse edges 28a, b extending obliquely, namely a distal transverse edge 28a and a proximal transverse edge 28b. Transverse to the outer terminal surfaces 24 are distal and proximal transverse surfaces 30a, b extending from the transverse edges 28a, b towards the elongated passage hole 10. It can be further seen that the elongated passage hole 10 extends in the longitudinal direction of the female branch 4 along the entire female terminal portion 6 and the two longitudinal ends 20a, b of the elongated passage hole 10 cross the distal and proximal transverse edges 28a, b, i.e. the distal longitudinal end 20a is distal to the distal transverse edge 28a and the proximal longitudinal end 20b is proximal to the proximal transverse edge 28b.

The male terminal portion 8 has two outer contact surfaces 32 extending essentially parallel to the pivot plane and facing away from each other. Four transverse surfaces 34, 36a, b extend transversely to the outer contact surfaces 32 on the male terminal portion 8 and connect the two outer contact surfaces 32. Two of the four transverse surfaces 34, 36a, b extend substantially in the longitudinal direction of the male branch 4 and are hereinafter referred to as longitudinal surfaces 34. The other two transverse surfaces represent a distal transverse surface 36a and a proximal transverse surface 36b, each extending obliquely to the longitudinal direction of the male branch 4.

In the terminal region 16 of the instrument 1 or respectively in its box-lock mechanism, the outer contact surfaces 32 of the male terminal portion 8 are rotatably in contact with the inner contact surfaces 18 of the female terminal portion 6. The hinge, via which the two branches 2, 4 are rotatably or pivotally held against each other, can be made via a known pin-receiving opening mechanism and is not shown in the figures. In this case, either the inner contact surfaces 18 may each have a pin which are arranged coaxially and each engage in a passage opening in the outer contact surfaces 32, or the outer contact surfaces 32 may each have a pin which are arranged coaxially and each engage in a passage opening on the inner contact surfaces 18. In particular, the two branches are connected to each other by a rivet (for example, a ball or step rivet).

The male and female terminal portions 6, 8 are each located between a distal effector portion 38 and a proximal handle portion 40. In the embodiment shown, the surgical instrument 1 is a surgical clamp and the effector portions 38 are curved gripping portions whose tips abut each other when the instrument is closed (see FIG. 5) and fix an object to be clamped, for example a surgical drape. The handle portions 40 of the two branches 2, 4 each have a handle loop 42 at their proximal ends, via which the user can grip and operate the instrument 1 in the manner of scissors. Directly distal to the handle loops 42, each branch 2, 4 has on the inside of the instrument a respective tongue 44 with three latch hooks 46 arranged one behind the other, which in the closed state of the instrument 1 are opposite each other and engage with each other in order to hold the branches 2, 4 of the instrument 1 against each other. The latch hooks 46 each have an inclined sliding surface and a latching surface rising essentially perpendicular to the longitudinal extension of the tongue 44. In order to close the latch closure formed in this way, the branches 2, 4 are manually pressed towards each other and the latch hooks 46 slide past each other along their inclined sliding surfaces. Each position behind the latching surfaces represents a closing position. For opening the instrument 1, the branches 2, 4 are manually (elastically) deflected from their pivot plane so that the latch hooks 46 are disengaged and the branches 2, 4 can be pivoted away from each other again.

In the preceding context, the inside of the instrument means the two sides of the branches 2, 4 that face each other when the instrument 1 is in the closed state. Consequently, the two sides of the branches 2, 4 that face away from each other when the instrument 1 is closed may be referred to as the outside of the instrument.

FIG. 1 further shows that the effector portions 38 each have an inner effector surface 48. The inner effector surface 48 is understood to be the surface of an effector portion 38, which, in the closed state of the instrument 1, faces the effector portion 38 of the other branch 2, 4. As can be seen in FIG. 1, the transition from the inner effector surface 48 of the female branch 2 to its distal transverse surfaces 30a at the terminal portion 6 is rounded. Moreover, the outer surfaces 50 of the effector portion 38 on the female branch 2 facing away from each other are flush with the outer terminal surfaces 24 of the female terminal portion 6. Also looking at the male branch 4, it can be seen that the transition from the inner effector surface 48 of the male branch 4 to its distal transverse surface 36a on the terminal portion 8 is rounded. The outer surfaces 52 of the effector portion 38 on the male branch 4 facing away from each other are not flush with the outer contact surfaces 32, but project substantially perpendicularly with respect thereto. As a result, the outer surfaces 52 of the effector portion 38 on the male branch 4 to the outer contact surfaces 32 of the male terminal portions 8 each form a step 54 projecting from the outer contact surface 32. This step 54 may be vertical, but may also be inclined or beveled or formed as a radius. As can be seen in FIG. 1, said steps 54 are longitudinally offset with respect to the distal transverse surface 36a of the male terminal portion 8, so that the respective common edges of the steps 54 and outer contact surfaces 32 do not coincide with the common edge of the inner effector surface 48 and the distal transverse surface 36a of the male terminal portion 8, but are arranged distally offset with respect thereto. In this way, a notch effect due to coinciding edges can be avoided.

Figure 2:
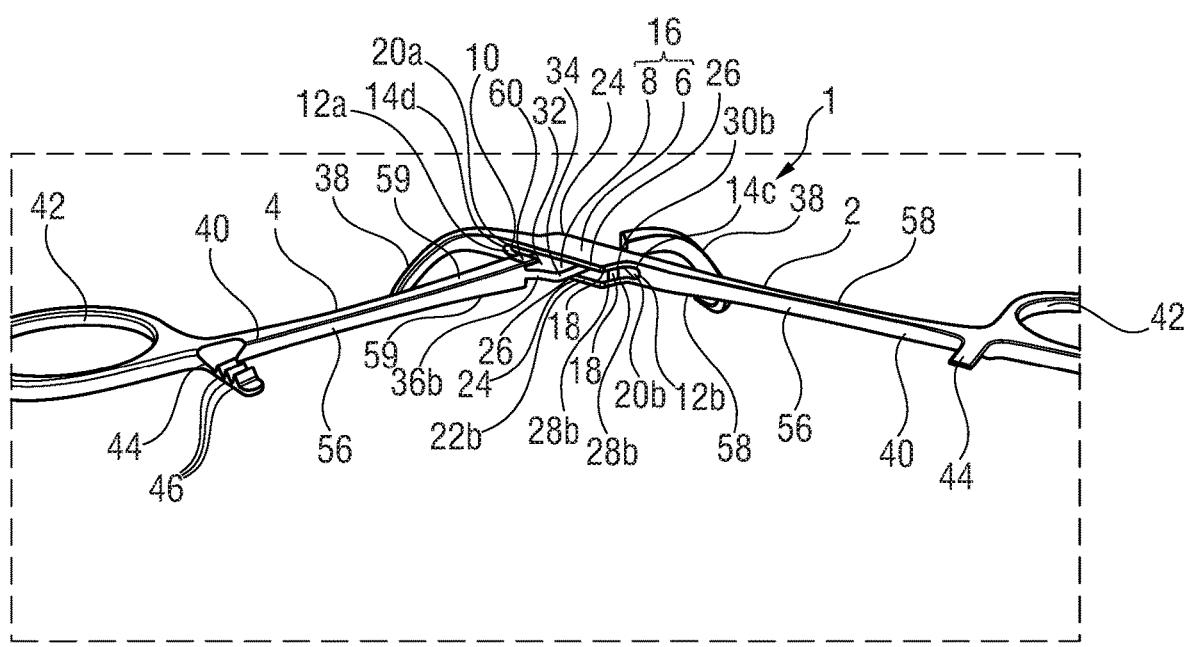
FIG. 2 shows a perspective rear view of the embodiment of the surgical instrument shown in FIG. 1 in the opened state.

In FIG. 2, the instrument 1 shown in FIG. 1 is shown in a perspective rear view. The second outer side 22b of the opening of the elongated passage hole 10 is shown here with longitudinal end surfaces 12a, b beveled in the direction of the second outer side 22b of the opening. FIG. 2 further shows that the transition from the inner handle surface 56 of the female branch 2 to its proximal transverse surfaces 30b on the terminal portion 6 is also rounded. The outer surface 58 of the handle portion 40 on the female branch 2, which face away from each other, are also flush with the outer terminal surfaces 24 of the female terminal portion 6. The inner handle surface 56 is to be understood in each case as the surface of a handle portion 40, which, in the closed state of the instrument 1, faces the handle portion 40 of the other branch 2, 4 in each case. Looking at the male branch 4, it can be seen in FIG. 2 that the transition from the inner handle surface 56 of the male branch 4 to its proximal transverse surface 36b is also rounded. The outer surfaces 59 of the handle portion 40 on the male branch 4 are also not flush with the outer contact surfaces 32, but project substantially perpendicularly with respect thereto. As a result, the outer surfaces 59 of the handle portion 40 on the male branch 4 with respect to the outer contact surfaces 32 form a respective step 60 projecting upwards from the outer contact surfaces 32 of the male terminal portion 8. This step 60 may also be vertical, but may also be inclined or beveled or may be formed as a radius. As already explained with respect to the effector portion 38 of the male branch 4, said steps 60 are also longitudinally offset with respect to the proximal transverse surface 36b of the male terminal portion 8, so that the respective common edges of the steps 60 and outer contact surfaces 32 do not coincide with the common edge of the inner handle surface 56 and proximal transverse surface 36b of the male terminal portion 8, but are arranged proximally offset with respect thereto in order to avoid a notch effect.

Figure 3:
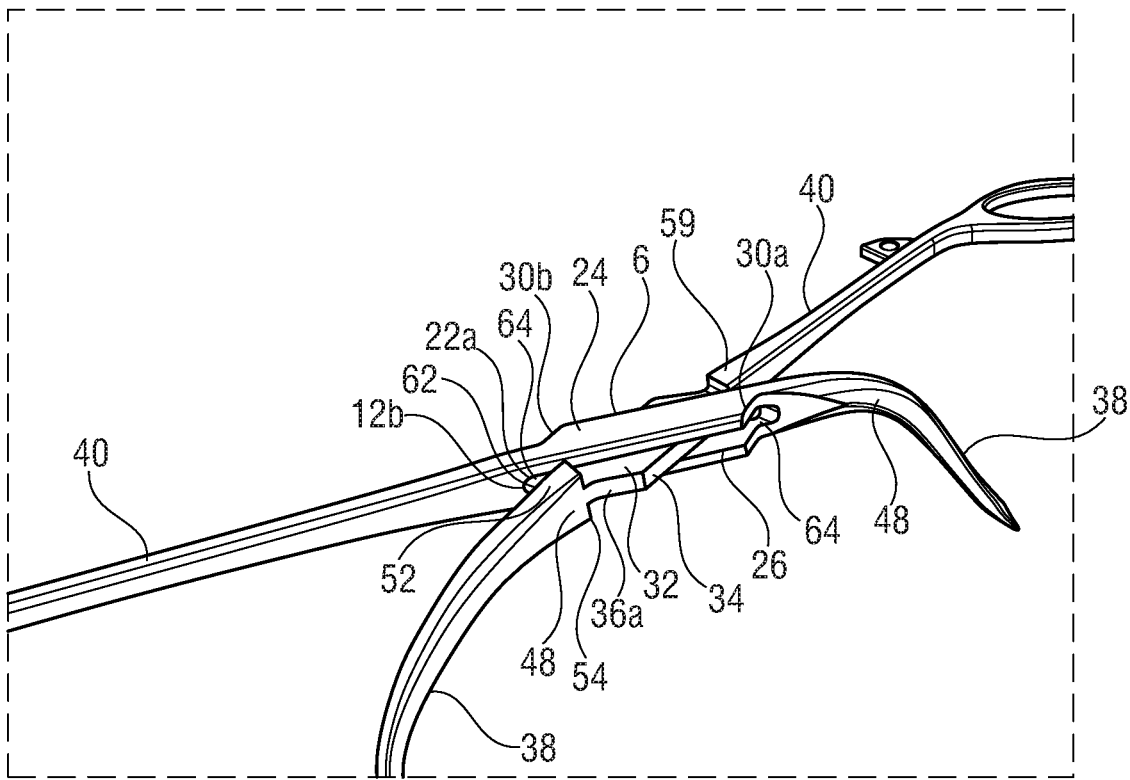
FIG. 3 shows a perspective front view of the embodiment of the surgical instrument shown in FIG. 1 in a maximum opened position.

FIG. 3 shows the embodiment of the surgical instrument 1 illustrated in FIG. 1 in a maximum opened position from a perspective frontal view. The shown relative position of the branches 2, 4 to each other can also be referred to as the fully opened position of the instrument 1 or respectively of the branches 2, 4. As becomes clear in particular by looking at the left part of FIG. 2, the elongated passage hole 10 is designed with such a length that the male branch 4 at the transition from effector portion 38 to the male terminal portion 8 abuts with its outer surface, specifically with its outer surface 62 on the outside of the instrument, against the first outer side 22a of the opening of the female terminal portion 6 without closing the elongated passage hole 10 at the first outer side 22a of the opening. Thus, a channel 64 for the passage of fluid exists in the terminal region 16 of the instrument 1 between the proximal longitudinal end surface 12b of the elongated passage hole 10 and a longitudinal surface 34 of the male terminal portion 6.

Figure 4:
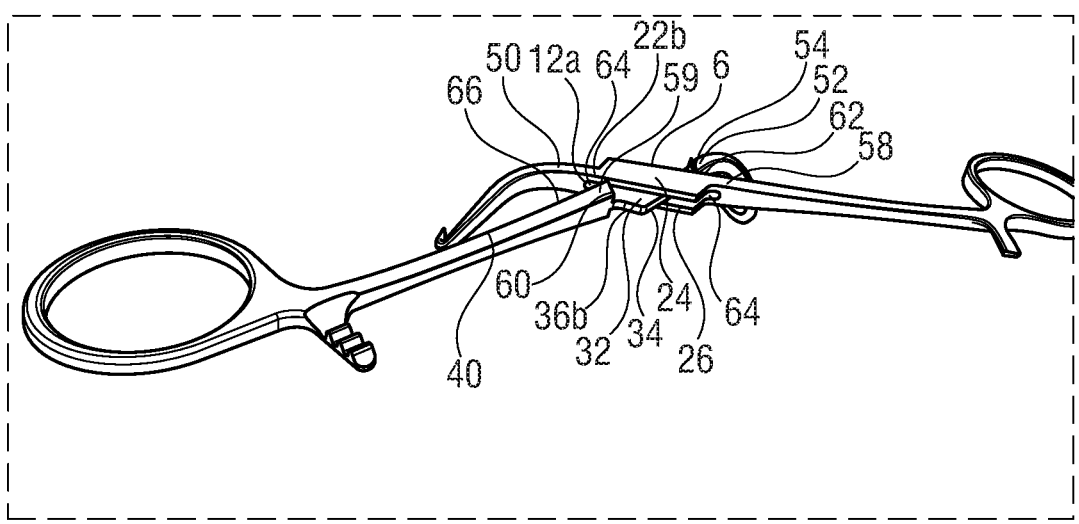
FIG. 4 shows a perspective rear view of the embodiment of the surgical instrument shown in FIG. 1 in a maximum opened position.

In FIG. 4, the embodiment of the surgical instrument 1 illustrated in FIG. 1 is shown in a maximum opened position from a perspective rear view. Analogous to the abutment position of the male branch 4 at the first outer side of the opening 22a of the female terminal portion 6, the male branch 4 abuts at its transition from the handle portion 40 to the terminal portion 8 with its outer surface, specifically with its outer surface 66 on the outside of the instrument, against the second outer side 22b of the opening of the female terminal portion 6, without closing the elongated passage hole 10 at the second outer side 22b of the opening, since also on this longitudinal side of the elongated passage hole 10 its length extends beyond the contact position of the male branch 4 at the outer side 22b of the opening and between its distal longitudinal end surface 12a and a longitudinal surface 34 of the male terminal portion 8, a channel 64 through which flow is possible is formed in the terminal region 16 of the instrument 1.

Figure 5:
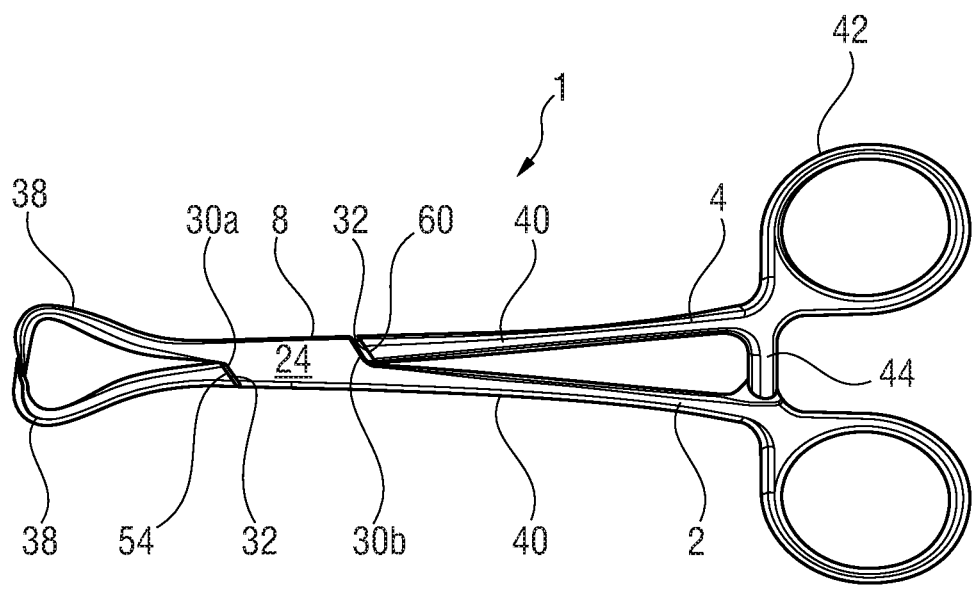
FIG. 5 shows a top view of the embodiment of the surgical instrument shown in FIG. 1 in a fully closed position.

FIG. 5 shows a top view of the surgical instrument 1 shown in FIG. 1 in a fully closed state. In this state, the two branches 2, 4 are maximally interlocked with each other, i.e. all three latch hooks 46 on one tongue 44 of each of the two handle portions 40 are engaged with the latch hooks 46 of the respective other tongue 44. The effector portions 38 of the two branches 2, 4 are in contact with each other directly distal to the terminal region 16 of the instrument 1, and the handle portions 40 of the two branches 2, 4 are in contact with each other directly proximal to the terminal region 16 of the instrument 1. In this view, it can be seen that the steps 54, 60 on both the effector portion 38 and the handle portion 40 of the male branch 4 are substantially parallel to each other and are spaced from the transverse edges or respectively transverse surfaces 30a, b of the female terminal portion 6 in the longitudinal direction of the instrument. It should be noted that although only the top view of the terminal region 16 of the instrument 1 is shown in FIG. 5, the terminal region 16 on its underside shows a functionally identical, albeit mirror-image, geometry or contact position of the branches 2, 4 against each other.

Figure 6:
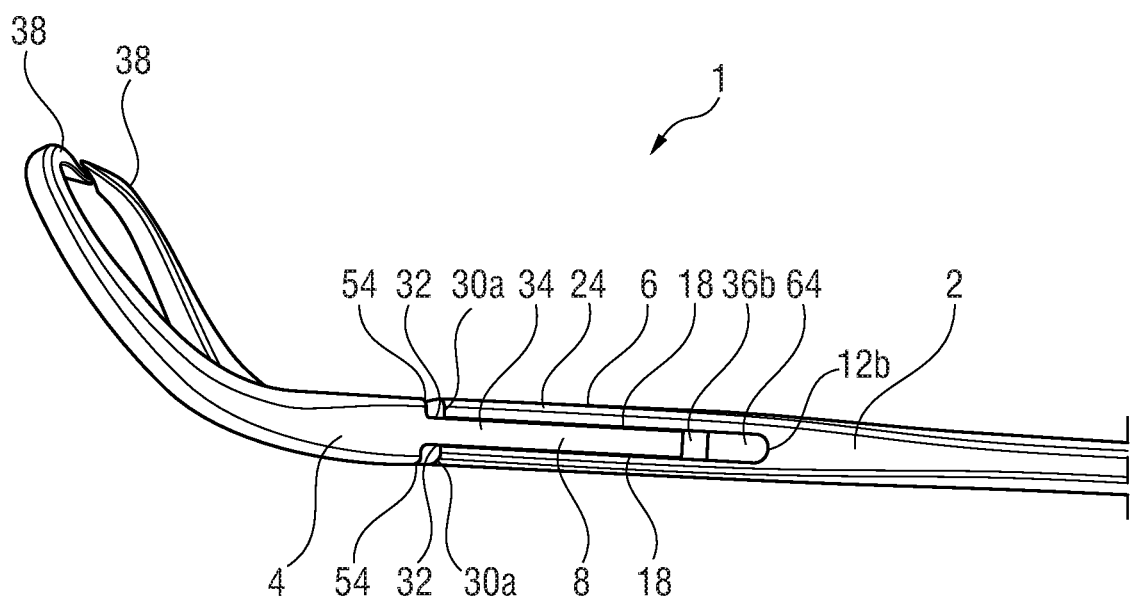
FIG. 6 shows a side view of the embodiment of the surgical instrument of FIG. 1 in a fully closed position.

Finally, FIG. 6 shows a side view of the surgical instrument 1 shown in FIG. 1 in a fully closed state. It can be seen again that the steps 54 from the outer contact surfaces 32 of the male terminal portion 8 to the effector portion 38 of the male branch 4 are spaced apart from the distal transverse edges or respectively transverse surfaces 30a of the female terminal portion 6. The outer contact surfaces 32 of the male terminal portion 8 abut the inner contact surfaces 18 of the elongated passage hole 10 of the female terminal portion 6. It can further be seen that even in the fully closed state, a channel 64 is present between the proximal longitudinal end surface 12b of the elongated passage hole 10 and the proximal transverse surface 36b of the male terminal portion 8, through which a fluid, in particular cleaning fluid, is able to flow. Even though in FIG. 6 only the channel 64 between the proximal longitudinal end surface 12b at the female terminal portion 6 and the proximal transverse surface 36b at the male terminal portion 8 and only the distance between the steps 54 to the effector portion 38 and the distal transverse surfaces 30a of the female terminal portion 6 are shown, it is understood due to the symmetrical geometry of the branches 2, 4, that also in the side view of the surgical instrument 1, which is not shown, there is a channel 64 between the distal longitudinal end surface 12a on the female terminal portion 6 and the distal transverse surface 36a on the male terminal portion 8 as well as a distance between the steps 30 to the handle portion 40 and the proximal transverse surfaces 30b of the female terminal portion 8.

With regard to the inner geometry of the elongated passage hole 10, it should also be noted that it takes the form of two intersecting part circles. Specifically, the elongated passage hole 10 is produced by first removing a part-circular volume from one of the two outer sides 22a, b of the openings, for example by milling, and then also removing a part-circular volume from the other outer side of the opening 22a, b, so that between the two outer sides 22a, b of the openings there is an opening in the form of an elongated hole, the longitudinal end surfaces 12a, b of which have a part-circular profile in the longitudinal direction of the branch 2 and run obliquely to the outer side 22a, b of the openings.

The invention claimed is:

1. A surgical instrument of cross-branched design having a female branch and a male branch, each having a terminal portion along their longitudinal extent, and the terminal portion of the female branch being pierced by a passage opening having a distal and a proximal longitudinal end surface, each having two outer edges and being adapted to receive the terminal portion of the male branch, so that the terminal portions form a box-lock mechanism in an assembly position of the surgical instrument, the passage opening having a length at which outer edges of the distal and proximal longitudinal end surfaces are exposed and are not covered by the male branch in all relative positions of the female branch and the male branch.

2. The surgical instrument according to claim 1, wherein the passage opening further forms two opposite inner contact surfaces connecting the distal and proximal longitudinal end surfaces, the terminal portion of the male branch forming two outer contact surfaces facing away from each other and outer transverse surfaces connecting the two outer contact surfaces to each other, so that in the box-lock mechanism in each case an inner contact surface and an outer contact surface are held rotatably against each other, and in all relative positions of the female branch and the male branch in each case between the distal and proximal longitudinal end surfaces and an outer transverse surface, a channel through which flow is possible is formed.

3. The surgical instrument according to claim 1, wherein the passage opening forms an elongated passage hole.

4. The surgical instrument according to claim 1, wherein the passage opening has two outer sides, and the distal and proximal longitudinal end surfaces are each beveled at least to one of the two outer sides in order to increase an opening cross-section at said one of the two outer sides.

5. The surgical instrument according to claim 2, wherein the terminal portions are each arranged between a distal effector portion and a proximal handle portion, wherein the distal effector portions have inner effector surfaces facing one another, and the proximal handle portions have inner handle surfaces facing one another, the outer transverse surfaces of the terminal portion of the male branch are a distal transverse surface, a proximal transverse surface, and two side surfaces oriented substantially parallel to each other, wherein the distal transverse surface adjoins the inner effector surface of the male branch and the proximal transverse surface adjoins the inner handle surface of the male branch, and transitions from the distal transverse surface to the inner effector surface form a distal rounding, and transitions from the proximal transverse surface to the inner handle surface form a proximal rounding.

6. The surgical instrument according to claim 5, wherein the distal effector portion and the proximal handle portion of the male branch each have two outer surfaces facing away from each other, which adjoin the outer contact surfaces of the terminal portion of the male branch and, at their transitions to the outer contact surfaces, they form steps with respect to the outer contact surfaces, wherein the steps on a side of the inner effector surface are arranged distal to the distal rounding, and the steps on a side of the inner handle surface are arranged proximal to the proximal rounding.

7. The surgical instrument according to claim 6, wherein the terminal portion of the female branch has two outer terminal surfaces extending substantially parallel to the inner contact surfaces, which, in a closed state of the instrument, are arranged at a distance from the outer surfaces of the handle portion and of the effector portion of the male branch.

* * * * *